US006461844B1

(12) United States Patent
Elbein et al.

(10) Patent No.: US 6,461,844 B1
(45) Date of Patent: Oct. 8, 2002

(54) LIVER GALNAC-1-PHOSPHATE KINASE

(75) Inventors: Alan D. Elbein; Richard R. Drake; Irena Patuszak, all of Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 888 days.

(21) Appl. No.: 08/697,199

(22) Filed: Aug. 21, 1996

Related U.S. Application Data

(60) Provisional application No. 60/002,617, filed on Aug. 22, 1995.

(51) Int. Cl.[7] ................................................. C12N 9/12
(52) U.S. Cl. ....................................................... 435/194
(58) Field of Search ................................ 435/194, 200, 435/208

(56) References Cited

FOREIGN PATENT DOCUMENTS

| WO | 97/08305 | * | 3/1997 |

OTHER PUBLICATIONS

Leloir et al. (1958) Arch. Biochem. Biophys., 74, "Phosphorylation of Acetylhexosamines", pp. 84–91.*
Maley et al. (1968) Biochem. J., 107, "The Metabolism of D–Galactosamine and N–Acetyl–D–Galactosamine in Rat Liver", pp. 637–644.*
Pastuszak et al. (1996a) J. Biol. Chem., 271(34), "Kidney N–Acetylgalactosamine (GalNAc)–1–Phosphate Kinase, A New Pathway of GalNAc Activation", pp. 20776–20782.*
Pastuszak et al. (1996b) J. Biol. Chem., 271(39), "Identification of the GalNAc Kinase Amino Acid Sequence", pp. 23653–23656.*

* cited by examiner

*Primary Examiner*—Jon P. Weber
(74) *Attorney, Agent, or Firm*—Benjamin Aaron Adler

(57) ABSTRACT

A new enzyme that phosphorylates GalNAc at position 1 to form GalNAc-α-1P was purified ~1275-fold from the cytosolic fraction of pig kidney, and the properties of the enzyme were determined. The kinase is specific for GalNAc as the phosphate acceptor and is inactive with GlcNAc, ManNAc, glucose, galactose, mannose, GalN, and GlcN. The native enzyme has a molecular mass of 48–51 kDa, and this enzyme is clearly separated from galactokinase by chromatography. The GalNAc kinase has a pH optimum between 8.5 and 9.0, and requires a divalent cation in the order $Mg^{2+}>Mn^{2+}>Co^{2+}$, with optimum $Mg^{2+}$ concentration at ~5 mM. The enzyme was most active with ATP as the phosphate donor, but slight activity was observed with ITP, acetyl-P, and phosphoenolpyruvate. Enzyme activity was highest in porcine and human kidney and porcine liver, and was low in most other tissues.

5 Claims, 7 Drawing Sheets

LIVER GALNAC-1-PHOSPHATE KINASE

This application claims benefit of Provisional Appln 60/002,617 filed Aug. 22, 1995.

BACKGROUND OF THE INVENTION

1. Field of the Invention

The present invention relates generally to the fields of enzymology and carbohydrate chemistry. More specifically, the present invention relates to purified, homogeneous liver GalNAc-1-P kinase and uses thereof.

2. Description of the Related Art

N-acetylgalactosamine (GalNAc) is an important sugar in complex carbohydrates because it is usually the sugar that links the carbohydrate chains to protein in mucins (1–3) and other O-linked oligosaccharides (4–6). In these glycoproteins, the linkage usually involves a GalNAc to serine or threonine attachment site. GalNAc is also found in many of the glycosphingolipids that are present in animal cell membranes (7,8), and is a major component of some proteoglycans such as chondroitin sulfates (9).

The current dogma on the formation and activation of GalNAc in animal cells is as follows (10):

1. Fructose-6-P+Glutamine→Glucosamine-6-P+glutamate
2. Glucosamine-6-P+Acetyl-CoA→GlcNAc-6-P+CoASH
3. GlcNAc-6-P⇌GlcNAc-1-P
4. GlcNAc-1-P+UTP⇌UDP-GlcNAc+PPi
5. UDP-GlcNAc⇌UDP-GalNAc The enzyme UDP-GlcNAc pyrophosphorylase was first partially purified from calf liver and from *Staphylococcus aureus* by Strominger and Smith, and various properties of the enzyme were determined. Those enzyme preparations utilized UDP-GalNAc as a substrate at about 2.8% of the rate of the phosphorolysis with UDP-GlcNAc, but it was not clear whether that activity was due to a contaminating pyrophosphorylase. With the partially purified enzyme, the rate of UDP-glucose pyrophosphorolysis was about 30% of the rate with UDP-GlcNAc. The pyrophosphorylase was also partially purified from calf brain and that enzyme also utilized UDP-glucose at about 36% of the rate with UDP-GlcNAc.

The prior art is deficient in the lack of a purification of the enzyme N-acetylgalactosamine kinase to homogeneity for specific uses. The present invention fulfills this longstanding need and desire in the art.

SUMMARY OF THE INVENTION

The present invention has demonstrated the presence in pig kidney and some other pig tissues of a new enzyme that phosphorylates free GalNAc in the 1-position to produce GalNAc-1-P. This enzyme has been extensively purified from the cytosol of kidney. The purified enzyme phosphorylates GalNAc, but not galactose, galactosamine, glucose, GlcNAc or glucosamine. This enzyme may represent part of a salvage pathway that allows the organism to reutilize the free GalNAc that arises from the turnover of O-linked glycoproteins and other complex carbohydrates.

In this regard, a UDP-HexNAc pyrophosphorylase from pig liver that catalyzes the formation of either UDP-GlcNAc from UTP and GlcNAc-1-P, or UDP-GalNAc from UTP and GalNAc-1-P (11) was recently purified. Thus, some pig tissues appear to have the necessary enzymes to convert free GalNAc to its "activated" form, i.e., UDP-GalNAc, for polymerization, without the intervention of UDP-GlcNAc.

In one embodiment of the present invention, there is provided an enzyme N-acetylgalactosamine kinase in isolated and purified form.

In another embodiment of the present invention, there is provided an enzyme that has a molecular weight of about 50 kilodaltons when analyzed by sodium dodecyl sulfate polyacrylamide gel electrophoresis, has an optimal pH of from about pH 8.5 to about 9.0, and wherein said enzyme catalyzes the phosphorylation of N-acetylgalactosamine and does not phosphorylate N-acetylglucosamine, N-acetylmannosamine, glucose, galactose, mannose, galactosamine and glucosamine.

In another embodiment of the present invention, there is provided polyclonal antiserum recognizing the enzyme of the present invention.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

The present invention shows an SDS-PAGE of GalNAc kinase at various stages of purification. The kinase was purified as indicated in Table I, and an aliquot of the enzyme preparation at each step was subjected to SDS-PAGE and stained with Coomassie blue to visualize the protein pattern. The present invention shows that the most purified enzyme preparation was incubated with various amounts of azido-ATP[$^{32}$P] and the samples were subjected to SDS-PAGE. The proteins were transferred to nitrocellulose membranes and exposed to film to detect the radioactive bands.

DETAILED DESCRIPTION OF THE INVENTION

Figure 1:
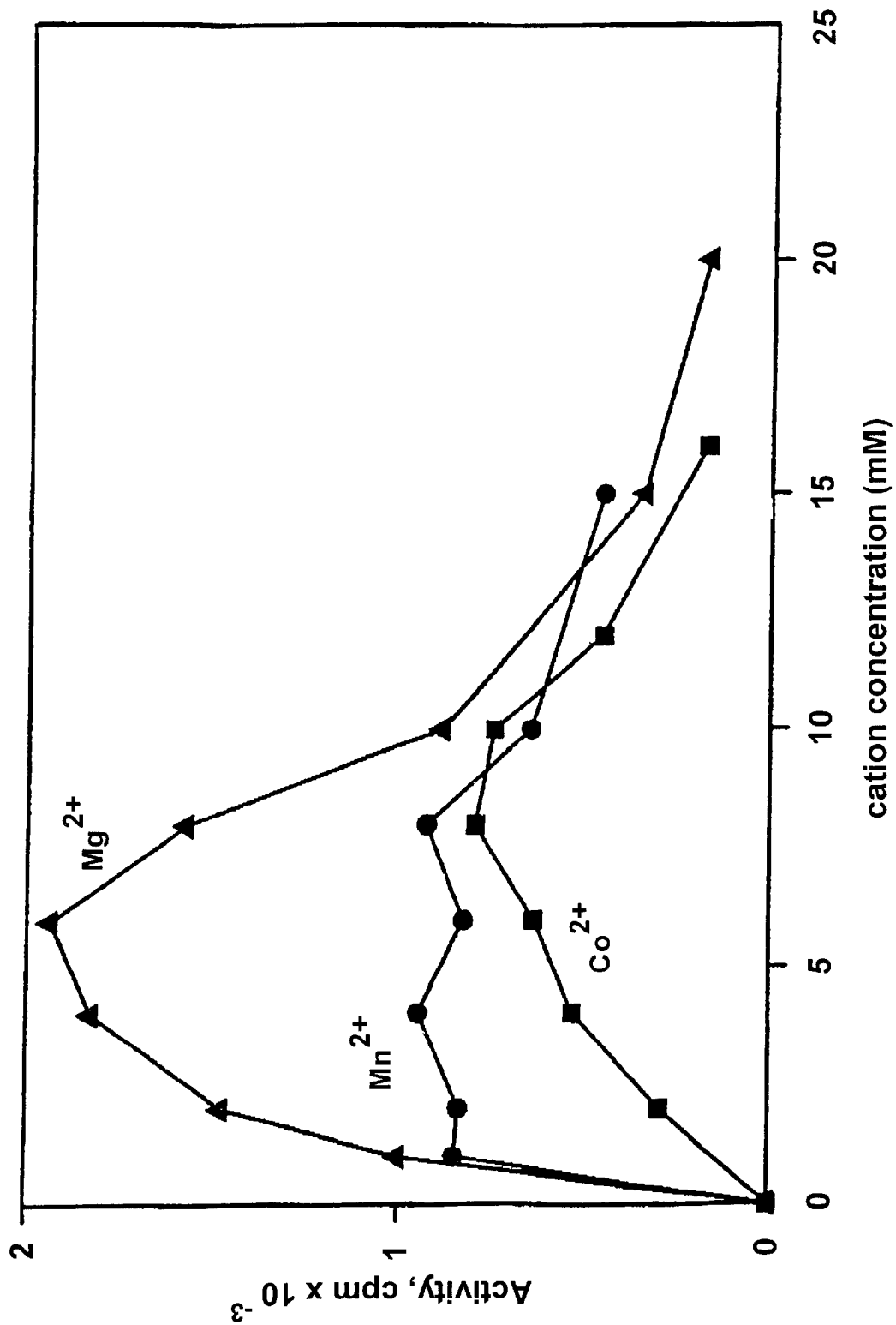
FIG. 1 illustrates the effect of various divalent cations on the GalNAc kinase. Various amounts of $Mg^{++}$, $Mn^{++}$, or $Co^{++}$ were added to incubations prepared as indicated below. The amount of GalNAc phosphorylated in each incubation by the purified enzyme was determined as described in the assay conditions. Various other cations, such as $Mo^{++}$, $Zn^{++}$, $Ni^{++}$, $Cu^{++}$, $Ca^{++}$ and $Fe^{+++}$, were tested at a number of concentrations and were found to be inactive.

In the present invention, there is provided a new enzyme that phosphorylates GalNAc in the one position to form GalNAc-1-P This enzyme was purified about 1400-fold from the cytosolic fraction of pig kidney, and the properties of the enzyme were determined. The kinase is quite specific for GalNAc as the phosphate acceptor and is inactive with GlcNAc, ManNAc, glucose, galactose, mannose, GalN and GlcN. This enzyme is clearly distinct from galactokinase which has no activity with GalNAc.

The GalNAc kinase has a pH optimum of about 8.5 to 9.0 and requires a divalent cation in the order $Mg^{++}>Mn^{++}>Co^{++}$, with optimum $Mg^{++}$ concentration at about 5 mM. The enzyme was most active with ATP as the phosphate donor. However, slight activity was observed with ITP, but not with other phosphate donors. Enzyme activity was highest in kidney and liver and was also detectable in spleen and lung, but not in pancreas, brain, aorta or heart.

The purified enzyme fraction was incubated with azido-ATP[$^{32}$P], exposed to UV light and run on SDS gels. A 50 kDa protein became labeled and the labeling showed saturation kinetics and was inhibited by unlabeled ATP. Based on chromatography on Sephacryl S-300, the native enzyme has a molecular weight of 48–51 kDa, indicating that the active kinase is a monomer. Enzyme activity was quite sensitive to inhibitors of SH group function such as pCMB and NEM and complete inhibition of activity occurred at a concentration of 0.04 mM pCMB. The product of the reaction was characterized as GalNAc-α-1-P by susceptibility of the phosphate group to mild acid hydrolysis, by its mobility on TLC and Dionex chromatography, and by high resolution NMR.

The following examples are given for the purpose of illustrating various embodiments of the invention and are not meant to limit the present invention in any fashion.

EXAMPLE 1

Materials

[6-$^3$]Glucosamine (40 Ci/mmol), [1-$^3$H]galactosamine (10–25 Ci/mmol), [6-$^3$H]galactose (20 Ci/mmol), [1-$^3$H]GalNAc (10–25 Ci/mmol), [6-$^3$H]GlcNAc (20–30 Ci/mmol), UDP-[6-$^3$H]GlcNAc (25 Ci/mmole) and UDP-[6-$^3$H]GalNAc (15 Ci/mmole) were purchased from American Radiolabeled Chemicals, Inc. Unlabeled sugars, sugar phosphates and nucleoside diphosphate sugars were obtained from Sigma Chemical Co. Various adsorbents were obtained from the following sources: DEAE cellulose (DE-52 diethylaminoethyl (DEAE) anion exchanger; pre-swollen microgranular)) from Whatman Chemical Separations, Ltd., Sephadex G-200 (dextran crosslinked with epichlorohydrin), Polybuffer Exchanger 94 (chromatofocusing for pH range 9–4) and Heparin-Sepharose (heparin (mucopolysaccharide of a repeating dimer of α-L-dipyranuronic acid 2-sulphate and 2-deoxy-2-sulphamino-α-D-glucopyranose 6-sulphate with a molecular weight range of 5,000–30,000) coupled to the Sepharose CL-6B matrix by the cyanogen bromide method) from Pharmacia LKB Biotechnology, Inc., Sephacryl S-300 (crosslinked co-polymer of allyl dextran and N,N'-methylenebisacrylamide), Blue-Sepharose (Sepharose CL-6B matrix), Pentyl-Sepharose (4% beaded agarose activated by cyanogen bromide), IDA-Sepharose (crosslinked 4% beaded agarose activated with epoxy), and Protein A-Sepharose (Sepharose CL-4B matrix activated by cyanogen bromide) from Sigma Chemical Co. PEI cellulose TLC plates were purchased from EM Science, cellulose TLC plates were from Kodak and silica gel TLC plates were from Merck. The following materials were obtained from Biorad: sodium dodecylsulfate (SDS), acrylamide, bisacrylamide, Coomassie blue, Protein assay reagent (Coomassie brilliant blue G-250 dye), hydroxyapatite, nitrocellulose, horseradish peroxidase-conjugated goat-antirabbit IgG (H+L) antibodies and Immobilon P membranes. All other chemicals were from reliable commercial sources and were of the best grade available.

EXAMPLE 2

GalNAc Kinase Assay

GalNAc kinase activity was assayed in incubation mixtures of 200 μl containing the following components: [$^3$H] GalNAc (10,000 cpm), 1 μmole of ATP, 2 μmoles of $MgCl_2$, 20 μmoles of Tris-HCl buffer, pH 7.5, and various amounts of the enzyme preparations to be assayed. Following an incubation for the appropriate time, the reaction was stopped by heating at 100° C. for 5 min., and the incubation mixture was applied to a column of DE-52. The column was washed with at least 5 column volumes of 10 mM $(NH_4)HCO_3$ buffer to remove unbound material, and then GalNAc phosphate was eluted with 500 mM ammonium bicarbonate. Aliquots of the wash and eluent were removed and assayed for their radioactive content by scintillation counting.

EXAMPLE 3

Purification of GalNAc Kinase: Preparation of Crude Extract

Fresh pig kidneys from a local slaughter house were generally used in these studies, but kidney could be quick frozen and used at a later time with equally good results. The kidneys were cut into small pieces and homogenized in Buffer A (10 mM Tris-HCl buffer, pH 7.8, containing 1 mM β-mercaptoethanol, 1 mM EDTA, 1 mM PMSF, 10% glycerol) in a Waring blender for 3–4 minutes. The homogenate was centrifuged at 12,000×g for 50 minutes, and the supernatant liquid was filtered through 4 layers of cheesecloth and centrifuged at 100,000×g for 45 minutes. The supernatant liquid was used in subsequent purification steps.

EXAMPLE 4

Ammonium Sulfate Precipitation

Solid ammonium sulfate was added to the above crude extract to reach 35% saturation, and after standing on ice for 15 minutes, the solution was centrifuged. The precipitate was discarded and solid ammonium sulfate was slowly added with stirring to the supernatant liquid to reach 60% saturation. After standing on ice for 15 min., the solution was centrifuged to obtain the precipitate which was dissolved in Buffer A at 25% of the original volume of the crude extract.

EXAMPLE 5

Phenyl-Sepharose Column Chromatography

The dissolved enzyme was applied to a 1.5×40 cm column of Phenyl-Sepharose that had been equilibrated with Buffer A, containing 1 M ammonium sulfate. The column was then washed with the equilibration buffer until the filtrate was almost colorless. The kinase was eluted from the column with a linear gradient of 1 M to 0 M ammonium sulfate in Buffer A. Active fractions were pooled and dialyzed against Buffer A, with several changes of the dialysis fluid during the 12 hour dialysis time.

EXAMPLE 6

DE-52 Cellulose Chromatography

De-52 cellulose was suspended in Buffer A, adjusted to pH 7.8 with dilute HCl, and the slurry was used to pack a 2×30 cm column. This column was then equilibrated with Buffer A. The dialyzed enzyme from the Phenyl-Sepharose column was applied to the DE-52 column, which was washed with Buffer A to remove unbound proteins. The enzyme was eluted with 300 ml of a linear gradient of 0 to 200 mM NaCl in Buffer A. The active fractions were pooled and concentrated to about 2 ml on an Amicon apparatus using a PM membrane.

EXAMPLE 7

Hydroxyapatite Column Chromatography

Active fractions from DE-52 were pooled and applied to a 1.5×10 cm column of hydroxyapatite. The column was washed with buffer A, and active enzyme was eluted with a gradient of phosphate buffer.

EXAMPLE 8

Gel Filtration Chromatography

The concentrated fraction eluted from the hydroxyapatite column was applied to a 1×50 cm column of Sephadex G-100 which had been equilibrated with Buffer B (20 mM HEPES buffer, pH 7.5, containing 1 mM β-mercaptoethanol, 1 mM EDTA, 0.1 mM PMSF and 10% glycerol). Four ml fractions were collected and every other fraction was assayed for protein and for GalNAc kinase activity.

EXAMPLE 9

Red-Sepharose Chromatography

The active enzyme fractions from Sephadex G-100 were pooled and applied to the Red-Sepharose 3000 CL column which was washed with Buffer B. The enzymatic activity emerged in the wash.

EXAMPLE 10

Aminohexyl-Agarose Chromatography

The active enzyme from Red-Sepharose was applied to an aminohexyl-Sepharose column that had been equilibrated with Buffer B. The column was washed with Buffer B, and bound enzyme was eluted with 5 mM ATP. Fractions containing active enzyme were pooled and concentrated to 3 ml on an Amicon apparatus.

EXAMPLE 11

Aminohexyl-Agarose-Galactosamine-Affinity Chromatography

The concentrated enzyme from step 7 was applied to a 0.9×3 cm column. The enzyme and affinity resin were allowed to stand for 1 hour to maximize adsorption and the column was washed with Buffer B to remove unbound protein. The enzyme was eluted with a linear gradient of 0 to 100 mM galactosamine. Active fractions were pooled, dialyzed and kept on ice for further use.

EXAMPLE 12

Native And SDS Gel Electrophoresis

Native PAGE was performed as described by Laemmli (12) with an 8% gel and a discontinuous buffer system, but under non-denaturing conditions. Two samples were run in parallel: One lane was stained with Coomassie blue to detect proteins and the other lane was cut into 1 cm pieces for the assay of enzymatic activity. SDS-PAGE was done as described (13). Prior to electrophoresis, protein samples were mixed with the same buffer (62 mM Tris-HCl, pH 6.8, 5% β-mercaptoethanol, 2% SDS, 10% glycerol and 0.002% bromophenol blue), and heated in a boiling water bath for 5 minutes.

EXAMPLE 13

Characterization of the Product

Large scale incubations were prepared with radioactive GalNAc in order to isolate sufficient amounts of product for characterization. These large scale incubations contained the same components as in the GalNAc kinase assay mixtures but were scaled up by a factor of ten. After incubation, the reactions were stopped by heating and the product was isolated by chromatography on a column of DE-52.

The radioactive material was examined for purity and characterization by TLC chromatography on cellulose plates in 70% ethanol: 1 M ammonium acetate, pH 7.5 (7:3), or in 70% ethanol: 1 M ammonium acetate, pH 3.5 (7:3). The product was subjected to HPLC on the Dionex apparatus, using a column to separate various sugar phosphates from each other. Sugar-1-phosphates were distinguished from sugar-6-phosphates by their susceptibility to acid hydrolysis in 0.05 N HCl at 100° C. Sugar-1-phosphates are rapidly hydrolyzed whereas sugar-6-phosphates are stable. The phosphorylated sugar product was characterized by NMR spectroscopy.

EXAMPLE 14

Purification of GalNAc Kinase

The GalNAc kinase was purified from the cytosolic fraction of pig kidney using the purification scheme described in the section above and outlined in Table I. Using this procedure, the kinase was purified about 1400-fold from crude extracts with a recovery of about 24%. The present invention shows the protein profiles at various stages of the purification procedure. It was demonstrated that the most purified enzyme fraction showed a single protein band on SDS-PAGE, and this band became intensely labeled when incubated with an ATP[$^{32}$P] photoaffinity probe. In addition, the amount of label in that band increased with increasing amounts of the probe, and the labeling was inhibited by adding unlabeled ATP, but not by other nucleotides. It should also be noted that the specific protein that became labeled had a molecular weight of about 50 kDa. Moreover, gel filtration of the native enzyme on Sephadex G-100 gave an activity peak in the region where proteins of about 48–51 kDa elute. Thus the native protein is probably a monomer of about 50 kDa molecular weight. Sufficient amounts of this protein band can be prepared to determine the amino acid sequence and to prepare antibodies.

TABLE I

Purification Procedure for GalNAc Kinase

| | Protein (mg) | Specific activity | Purification (fold) (umol/min/ug) | Yield (%) |
|---|---|---|---|---|
| Extract | 9870 | 0.0008 | 1 | 100 |
| Ammomium Sulfate | 4900 | 0.001 | 2 | 100 |
| Phenyl-sepharose | 1200 | 0.008 | 10.6 | 100 |
| DE-52 | 136 | 0.042 | 52.8 | 71.5 |
| Hydroxyapatite | 34 | 0.105 | 131.1 | 44.6 |
| Sephadex G-100 | 5.5 | 0.219 | 273.8 | 42.5 |
| Red-sepharose | 6. | 0.315 | 394.3 | 23.7 |
| Aminohexyl-agarose | 1.6 | 1.166 | 1458.3 | 23.6 |

EXAMPLE 15

Sugar Specificity of the GalNAc Kinase Compared to Yeast Galactokinase

The specificity of the GalNAc kinase for the sugar substrate was determined as shown in Table II. A variety of sugars were tested and in each case the specific radioactivity of the labeled sugar was adjusted with unlabeled material so that all were of the same specific activity in order to allow a true comparison of their ability to serve as substrates for the kinase. The amount of radioactivity that bound to DE-52 and was eluted with (NH$_4$)HCO$_3$ was taken as a measure of phosphorylation by the enzyme. Table II clearly demonstrates that only GalNAc could serve as a substrate, and essentially no phosphorylation was observed with any other sugar. Galactose and perhaps galactosamine did show slight activity, but in either case it was only 1% of the activity observed with GalNAc. These data indicate that this enzyme is very specific for GalNAc.

TABLE II

Sugar Specificity of GalNAc Kinase

| Sugar | Amount of Enzyme ($\mu$l) | Radioactivity Incorp. (cpm) |
|---|---|---|
| GalNAc | 4 | 14,094 |
| | 8 | 18,448 |
| GalN | 4 | 449 |
| | 8 | 468 |
| Gal | 4 | 301 |
| | 8 | 442 |
| GlcNAc | 4 | 135 |
| | 8 | 147 |
| GlcN | 4 | 189 |
| | 8 | 206 |
| Glucose | 4 | 124 |

TABLE II-continued

Sugar Specificity of GalNAc Kinase

| Sugar | Amount of Enzyme ($\mu$l) | Radioactivity Incorp. (cpm) |
|---|---|---|
| | 8 | 111 |
| ManNAc | 4 | 475 |
| | 8 | 89 |

Galactokinase is an enzyme known to phosphorylate galactose in the one position. Table III shows the sugar specificity of the yeast galactokinase (purchased from Sigma Chemical Co). It can be seen that this enzyme was very active when galactose was the substrate, but it also had slight activity when glucose and galactosamine were tested as substrates. However, there was no phosphorylation observed when GalNAc was tested as the substrate instead of galactose. The specificity of the galactokinase and the GalNAc kinase indicate that they are two different enzymes.

TABLE III

Sugar Specificity Of Yeast Galactose Kinase

| SUGAR | Enzyme (ul) | Radioactivity Incorporated | ($\Delta$ cpm) |
|---|---|---|---|
| Galactose | 0 | 65 | — |
| | 2 | 6900 | 6835 |
| | 4 | 7530 | 7465 |
| Glucose | 0 | 240 | — |
| | 2 | 335 | 95 |
| | 4 | 590 | 350 |
| Galactosamine | 0 | 127 | — |
| | 2 | 300 | 173 |
| | 4 | 440 | |
| glucosamine | 0 | 157 | — |
| | 2 | 135 | 0 |
| | 4 | 150 | 0 |
| GlONAC | 0 | 74 | — |
| | 2 | 133 | 60 |
| | 4 | 84 | 10 |
| GalNAc | 0 | 72 | — |
| | 2 | 37 | 0 |
| | 4 | 83 | 11 |

EXAMPLE 16

Specificity for Nucleoside Triphosphates as the Phosphate Donor

A variety of nucleoside mono-, di- and triphosphates were tested as phosphate donors for the GalNAc kinase as shown in Table IV. ATP was by far the best phosphate donor, but some activity was observed with ITP. Activity was also observed with GTP, CTP, CDP and ADP, but this activity was only slightly above background levels and is probably not real. In some of these cases, the activity may be due to trace amounts of ATP in the other nucleotide preparations. No activity was observed with acetylphosphate or phosphoenolpyruvate as phosphate donors.

TABLE IV

Phosphate Donor Specificity of GalNAc Kinase

| Nucleotide Added (at 5 mM) | Radioactivity in Sugar-P | Specific Activity (nmol/mg) |
|---|---|---|
| ATP | 10,195 | 160.0 |
| ADP | 260 | 4.0 |
| CTP | 370 | 5.8 |
| CDP | 490 | 7.6 |
| GTP | 300 | 4.7 |
| GDP | 10 | 0.1 |
| ITP | 900 | 14.1 |
| UTP | 180 | 2.8 |
| UDP | 30 | 0.5 |
| PEP | | |
| Acetyl-P | | |

EXAMPLE 17

Requirement for Divalent Cation for Activity

The purified enzyme was essentially inactive in the absence of a divalent cation as seen in FIG. 1. The addition of $Mg^{++}$ greatly stimulated the activity, and maximum activity occurred at 6 mM $Mg^{++}$. Other divalent cations, such as $Mn^{++}$ and $Co^{++}$ were also somewhat stimulatory, but much less so than $Mg^{++}$. Thus, optimum activity was observed in the presence of 2–8 mM $Mn^{++}$, or 10 mM $Co^{++}$ but this maximum activity was only about 50% of that seen with optimum concentrations of $Mg^{++}$. Various other cations were tested at a variety of concentrations, including $Mo^{++}$, $Zn^{++}$, $Ni^{++}$, $Cu^{++}$, $Ca^{++}$ and $Fe^{+++}$, and all of these were inactive in stimulating the kinase.

EXAMPLE 18

Effect of pH and Substrate Concentration on Activity

Figure 2:
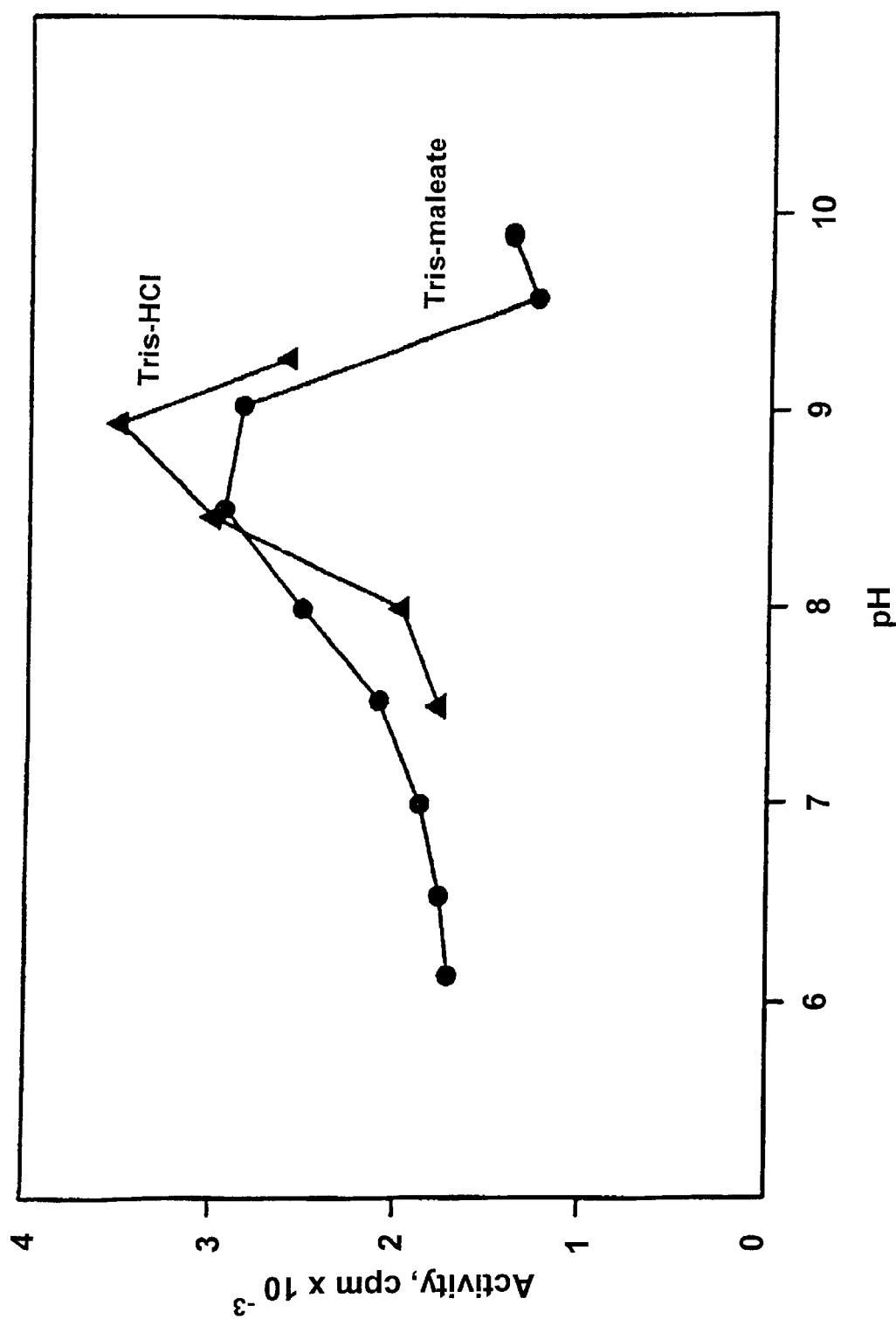
FIG. 2 shows the effect of pH of the incubation mixture on GalNAc kinase activity. Incubations were prepared as described below except that the pH was varied as indicated in the Figure. Two different buffers, Tris-HCl and Tris-maleate at 50 mM concentrations, were tested for their effect. Phosphorylation of GalNAc by the purified kinase was measured as described.
Figure 3A:
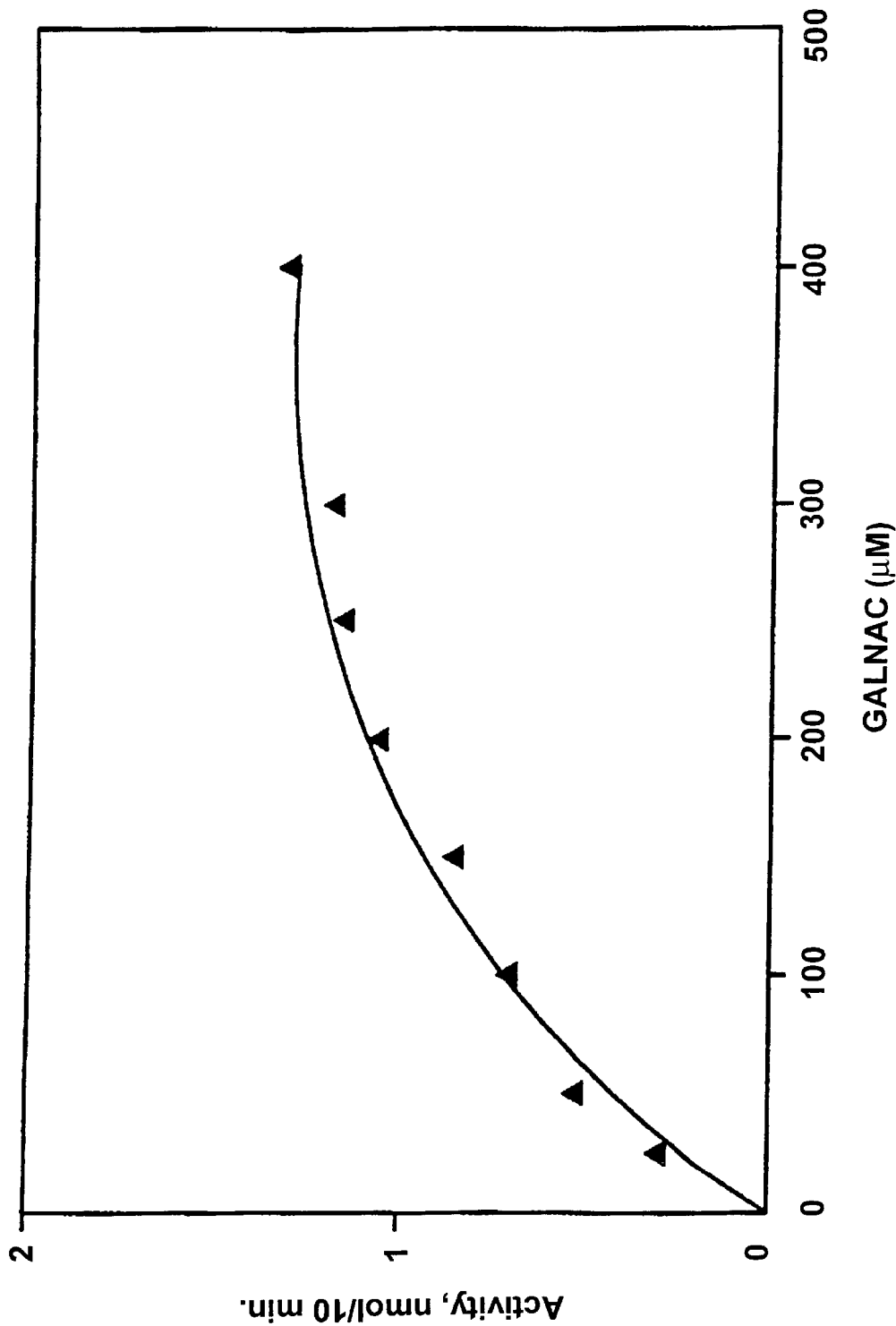
In FIG. 3A, various amounts of GalNAc were added to otherwise standard incubation mixtures containing 300 μM ATP, and the amount of GalNAc phosphorylated by the purified enzyme was determined.
Figure 3B:
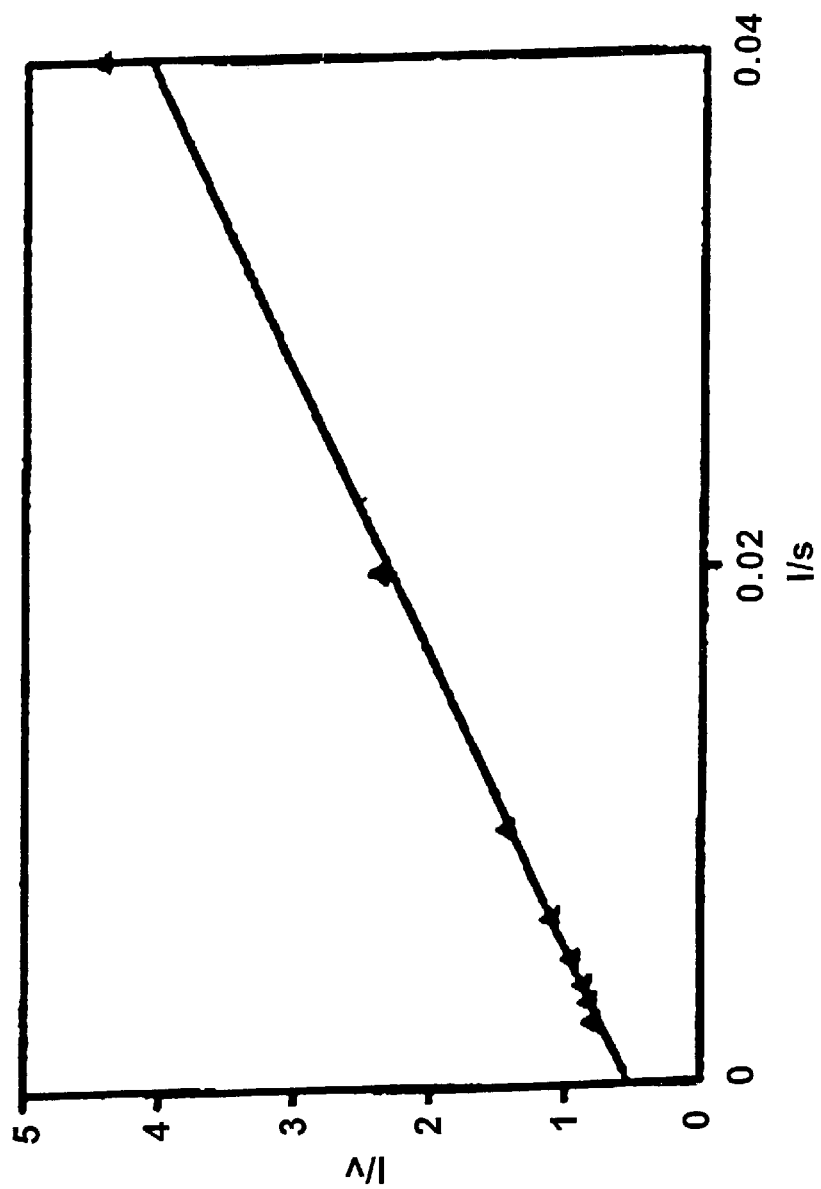
In FIG. 3B, the data was replotted by the method of Lineweaver and Burk.
Figure 3C:
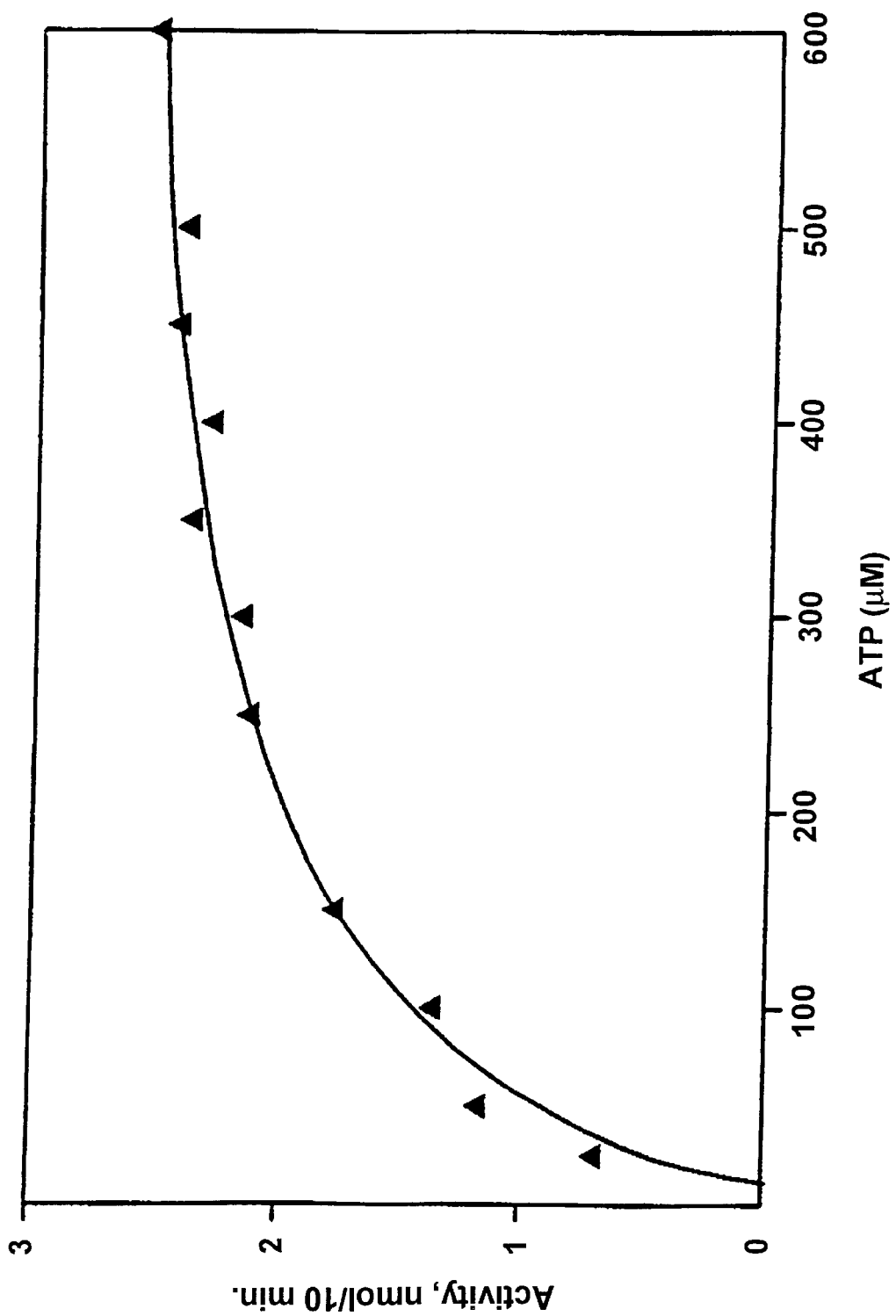
In FIG. 3C, various amounts of the other substrate, ATP, were added to otherwise standard incubation mixtures containing saturating (300 μM) levels of GalNAc and the amount of phosphorylation of GalNAc by the purified enzyme was determined. The data was also plotted by the method of Lineweaver and Burk as shown in FIG. 3D.
Figure 3D:
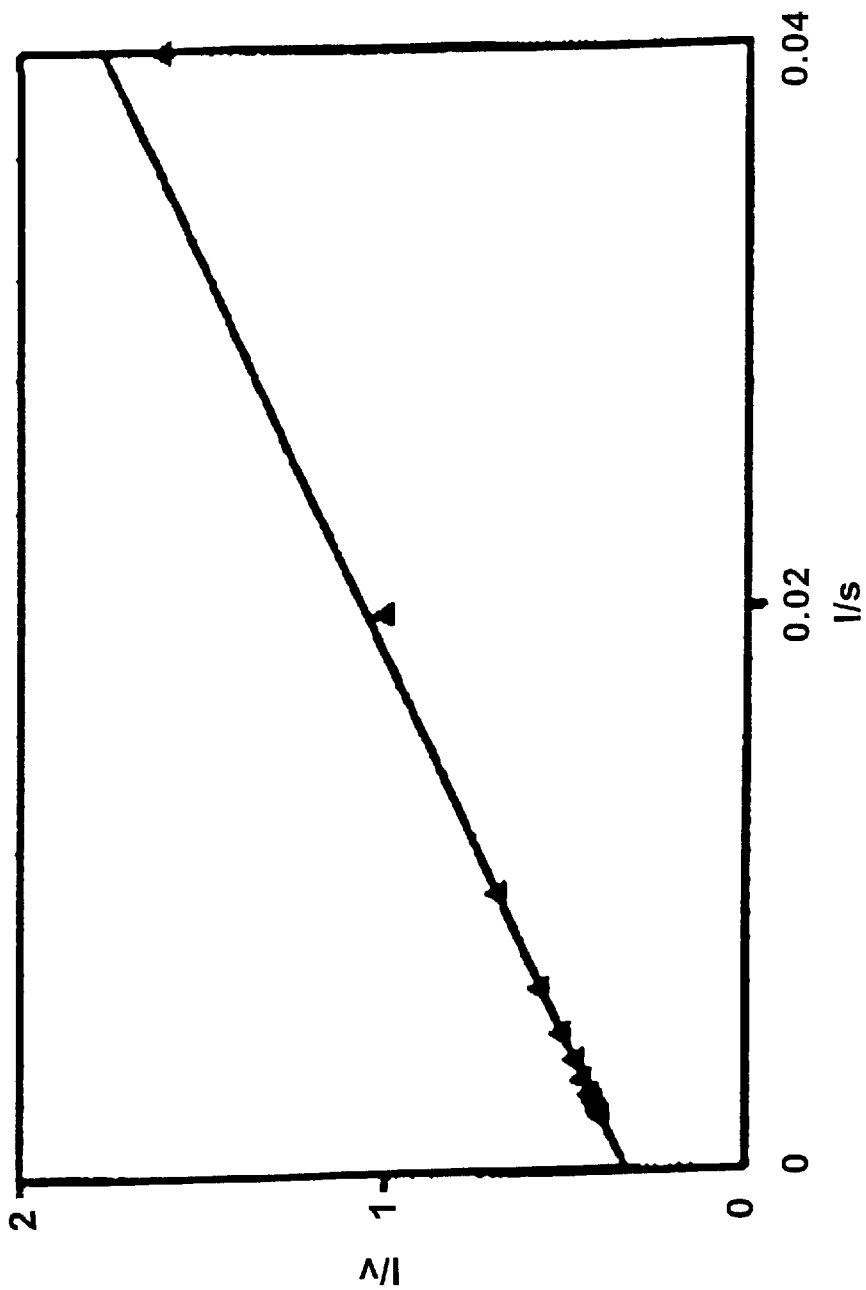
FIG. 3 shows the effect of substrate concentration on GalNAc kinase activity.

The effect of pH of the incubation mixture on enzymatic activity was examined in two different buffers as shown in FIG. 2. Activity was somewhat better in Tris-HCl buffer where optimum activity occurred at pH 8.9. In Tris-maleate buffer, activity was somewhat lower and the pH optimum was somewhat broader, occurring at pH 8.5–8.9.

The effect of concentration of the various substrates on the formation of GalNAc-1-P is shown in FIG. 3. FIG. 3A demonstrates the dependence of the reaction rate on the concentration of GalNAc up to about 250 μM and the $K_m$ for GalNAc was calculated to be $5 \times 10^{-5}$ M (FIG. 3B). FIG. 3C shows the effect of concentration of ATP on the formation of GalNAc-1-P. The reaction rate was proportional to concentration of ATP up to about 400 μM, and the $K_m$ for ATP was calculated to be $1 \times 10^{-4}$ M (FIG. D).

EXAMPLE 19

Tissue Distribution of the GalNAc Kinase

In order to determine the distribution of this enzyme activity in various pig tissues, crude extracts were prepared from a variety of freshly collected pig tissues and several different amounts of each extract was assayed for its ability to phosphorylate GalNAc. Table V presents the results of these screens. Pig kidney showed the best total activity and the highest specific activity, while pig liver was the next best tissue with about ½ of the total activity. Some activity was also observed in spleen and lung, but other tissues such as pancreas, brain, aorta and heart were considered to be devoid of this enzyme.

TABLE V

Tissue Distribution of GalNAc Kinase

| Tissue | Radioactivity Incorporated (cpm) 5 μl extract | Radioactivity Incorporated (cpm) 10 μl extract | Specific Activity (cpm/mg protein) |
|---|---|---|---|
| Liver | 1220 | 2040 | 5.13 |
| Kidney | 2120 | 4600 | 9.4 |
| Spleen | 960 | 2040 | 2.6 |
| Lung | 330 | 850 | 1.9 |
| Pancreas | 380 | 360 | 0.65 |
| Brain | 460 | 270 | — |
| Aorta | 480 | 270 | — |
| Heart | 80 | 60 | — |

EXAMPLE 20

Effect of Various Inhibitors of Sulfhydryl Groups on GalNAc Activity

In order to determine whether sulfhydryl groups are necessary for catalytic activity, the effects of various compounds known to react with and inactivate sulfhydryl groups, were examined on the kinase activity. The data from these experiments are presented in Table VI. It can be seen that p-chloromercuribenzoate (pCMB) was a very effective inhibitor of the enzymatic activity and caused over 70% inhibition at a concentration of 0.02 mM, and complete inhibition at 0.04 mM. N-ethylmaleimide was also inhibitory but required much higher concentrations (0.5 mM) for 90% inhibition, while iodoacetamide (IAA) was only effective as an inhibitor at concentrations above 1 mM.

TABLE VI

Effect of Various Sulfhydryl Reagents on GalNAc Kinase Activity

| Inhibitor Concentration (mM) | Activity (cpm in Sugar-P) in the presence of NEM | IAA | pCMB |
|---|---|---|---|
| 0 (Control) | 8700 | 8700 | 8700 |
| 0.02 | — | — | 2660 |
| 0.04 | — | — | 250 |
| 0.06 | — | — | 30 |
| 0.1 | 9050 | 8260 | 20 |
| 0.25 | — | — | 50 |
| 0.5 | 805 | 7660 | — |
| 1 | 40 | 5490 | — |
| 2 | 0 | 2170 | — |
| 4 | 0 | 658 | — |

EXAMPLE 21

Characterization of the Product

Since most sugar kinases phosphorylate the hydroxymethyl carbon at C6 or C5, it was important to determine the location of the phosphate group on the sugar, and to be certain that the sugar product was still GalNAc. Thus, large scale incubations were prepared, and the product was isolated as indicated above and purified by ion exchange and thin layer chromatography. A single, symmetrical radioactive peak was obtained from the DE-52 column, and this peak emerged in the same area as the GlcNAc-1-phosphate standard. In addition, a single radioactive band was detected on TLC plates.

Figure 4:
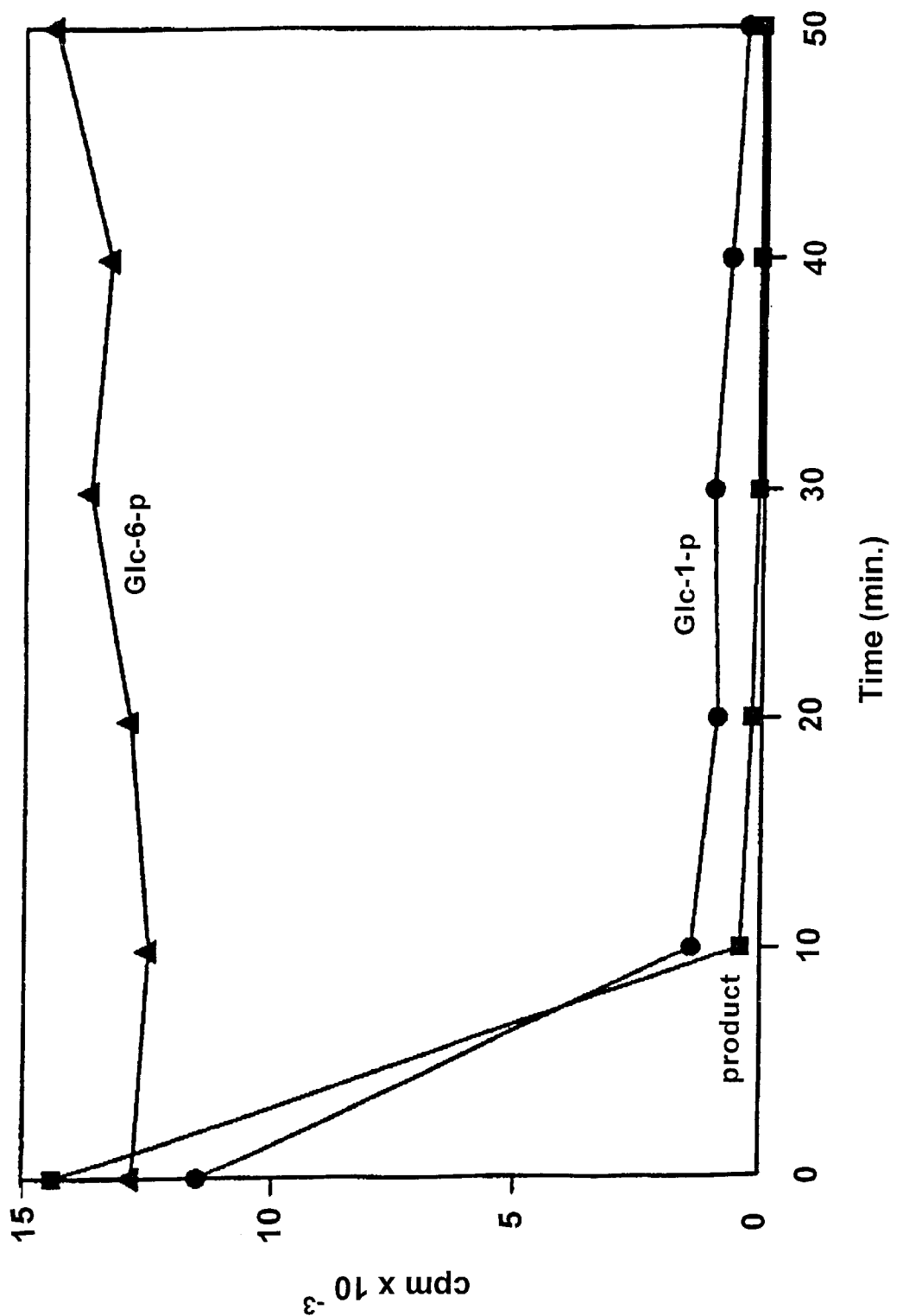
FIG. 4 shows the acid lability of the phosphate group on the GalNAc-P product. A large amount of the radioactive product formed by the GalNAc kinase was isolated and purified on a DE-52 column, and this product was suspended in 0.05 N HCl and placed in a hot water bath at about 95° C. At various times, aliquots of the reaction mixture were removed, cooled, neutralized and passed through a column of DE-52 to determine whether the $^3$H-GalNAc had lost its charge. Standards of Glc-6-P, Glc-1-P, GalNAc-1-P and GlcNAc-6-P were also subjected to the same hydrolysis conditions and were tested for their susceptibility to loss of phosphate.

The radioactive product from the ion exchange columns was suspended in 0.05 N HCl and heated at 100° C. for various periods of time. An aliquot of the reaction mixture was removed at each of the times shown in FIG. 4, and passed through a column of DE-52. The amount of radioactivity that emerged in the wash was taken as a measure of removal of the phosphate group. FIG. 4 shows that the GalNAc-P produced by the purified kinase was very susceptible to acid hydrolysis and almost all of the phosphate was removed within the first 10 minutes of hydrolysis, as was also the case for the glucose-1-phosphate and GlcNAc-1-phosphate standards. On the other hand, glucose-6-phosphate and GlcNAc-6-phosphate were quite stable to the hydrolysis conditions, and there was essentially no loss in their binding to the DE-52 columns even after 50 minutes. Thus, the phosphate group on the GalNAc-phosphate appears to be in the one position.

In order to be certain that the sugar was still GalNAc, the product of mild acid hydrolysis was identified by TLC and by HPLC. The radiolabeled sugar was mixed with unlabeled GalNAc and subjected to Dionex chromatography. Fractions were collected and their radioactive content was determined, whereas unlabeled sugars were determined by amperometric detection. The radioactivity emerged in the same position as authentic GalNAc (about 17.08 min) and was clearly separated from GlcNAc (15.78 min.). The radioactive sugar also migrated with authentic GalNAc, and not GlcNAc, on TLC plates in several solvents that separate these two aminosugars from each other, as well as from ManNAc (data not shown). In order to determine the anomeric configuration of the phosphate group, the GalNAc-1-phosphate was subjected to $D_2O$-NMR analysis.

Thus, the present invention provides the enzyme N-acetylgalactosamine kinase in isolated and purified form. Preferably, the enzyme is isolated and purified to homogeneity from pig liver. More preferably, the enzyme is isolated and purified to homogeneity from pig kidney. Most preferably, the enzyme is isolated and purified to homogeneity from the cytosolic fraction of said kidney.

The enzyme of the present invention wherein said enzyme has a molecular weight of about 50 kilodaltons when analyzed by sodium dodecyl sulfate polyacrylamide gel electrophoresis, has an optimal pH of from about pH 8.5 to about 9.0, and wherein said enzyme catalyzes the phosphorylation of N-acetylgalactosamine and does not phosphorylate N-acetylglucose, N-acetylmannose, glucose, galactose, mannose, N-Galactose and N-Glucose.

Generally, the enzyme of the present invention has a greater activity in the presence of magnesium than either manganese or cobalt. Preferably, the enzyme requires magnesium for optimal activity. Furthermore, the enzyme activity is highest when ATP is the phosphate donor. As shown herein the enzyme activity is significantly inhibited by sulhydryl group inhibitors. In another embodiment of the present invention is directed to polyclonal antiserum recognizing the GalNAc-1-Phosphate Kinase.

The present invention reports the identification and purification of a new phosphorylating enzyme in pig kidney and pig liver that transfers a phosphate group from ATP to GalNAc to form GalNAc-α-1-phosphate. Previous studies by Maley and coworkers (14) demonstrated the formation of GalNAc-1-phosphate from GalNAc and ATP by a crude extract of rat liver, but it was not clear from those studies whether that activity was due to the enzyme galactokinase, or to another kinase that could utilize GalNAc as a substrate.

More recently, a very interesting and useful CHO cell mutant, referred to as IdlD, was isolated and shown to be missing the enzyme that converts UDP-GlcNAc to UDP-GalNAc, i.e., the UDP-GalNAc 4-epimerase (15). This mutant, when grown in the absence of GalNAc or galactose, is defective in both O-linked and N-linked glycosylation because it cannot synthesize the necessary precursors, UDP-galactose and UDP-GalNAc. However, supplementation of the medium with free galactose and GalNAc allow it to produce normal N- and O-linked glycoproteins (16,17). The authors suggested that these cells contain another "scavanger" pathway that involves a kinase and a pyrophosphorylase for the production of the nucleoside diphosphate sugar precursors. However, these enzymes were not demonstrated in the present invention, nor were their specificities determined.

Previous studies have identified a UDP-HexNAc pyrophosphorylase in pig liver and pig kidney that could condense GalNAc-1-phosphate and UTP to produce UDP-GalNAc (11). In contrast to the previously reported UDP-GlcNAc pyrophosphorylases that had very low activity towards UDP-GalNAc (3%) as compared to UDP-GlcNAc (100%) (18,19), the pig liver and kidney UDP-HexNAc pyrophosphorylase prefers GalNAc-1-phosphate and UDP-GalNAc as substrates over GlcNAc-1-phosphate and UDP-GlcNAc. Based on the specificity of the GalNAc kinase for GalNAc but not galactose, and the preference of the UDP-HexNAc pyrophosphorylase for GalNAc-1-phosphate rather than GlcNAc-1-phosphate, it seems likely that these two enzymes do represent a specific salvage mechanism to reutilize GalNAc that is produced in kidney and liver by the turnover of O-linked glycoproteins.

Thus, there now appears to be two different mechanisms for producing UDP-GalNAc. The major pathway would be from fructose-6-phosphate via GlcNAc-6-phosphate and UDP-GlcNAc to form UDP-GalNAc by the UDP-galactose (GalNAc) 4-epimerase. The second pathway is the one described by the present invention with the GalNAc-1-phosphate kinase and the UDP-GalNAc pyrophosphorylase. This second pathway would mostly depend on the production of GalNAc from the turnover of O-linked glycoproteins and glycolipids. It will be interesting to determine whether tissue culture cells have these enzymes and can use them to produce UDP-GalNAc.

The following references were cited herein:

1. Devine, P. L. and McKenzie, I. F. C. (1992) Bioessays, 14, 619–625.
2. Carraway, K. L. and Hull, S. R. (1991) Glycobiology 1, 131–138.
3. Rose, M. C. (1992) Am. J. Physiol. Lung Cell. Mol. Physiol. 263, L413–L429.
4. Sadler, et al., (1979) J. Biol. Chem. 254, 661–667.
5. Davis, et al., (1986) J. Biol. Chem. 261, 2828–2838.
6. Fukuda, et al., (1989) Blood, 73, 84–89.
7. Ilyas, et al., (1985) Proc. Natl. Acad. Sci., USA, 82, 6697–6670.
8. Hakomori, S. (1981) Annu. Rev. Biochem. 50, 733–764.
9. Ruoslahti, E. (1988) Annu. Rev. Cell Biol. 4, 229–255.
10. Davidson, E. (1966) in "The Aminosugars", (E. Balazs and R. Jeanloz, eds), pp. 2–43 Academic Press, NY.
11. Szumilo, et al., (1996) J. Biol. Chem. 271, 13147–13154.
12. Laemli, U. K. (1970) Nature 227, 680–685.
13. Kaushal, et al., (1990) Biochemistry 29, 2168–2176.

14. Maley, et al., (1968) Biochem. J. 107, 637–644.
15. Kingsley, et al., (1986) Cell 44, 749–759.
16. Matzuk, et al., (1987) Proc. Natl. Acad. Sci. USA 84, 6354–6358.
17. Reddy, et al., (1989) J. Biol. Chem. 264, 17329–17336.
18. Strominger, et al., (1959) J. Biol. Chem. 234, 1822–1827.
19. Pattabiraman, et al., (1961) Biochim. Biophys. Acta 50, 129–134.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. The enzyme N-acetylgalactosamine kinase in isolated and purified form, wherein said enzyme is isolated from a tissue selected from the group consisting of pig liver and pig kidney and wherein said enzyme has a molecular weight of about 50 kilodaltons when analyzed by sodium dodecyl sulfate polyacrylamide gel electrophoresis, has an optimal pH of from about pH 8.5 to about 9.0, and wherein said enzyme catalyzes the phosphorylation of N-acetylgalactosamine and does not phosphorylate N-acetylglucosamine, N-acetylmannosamine, glucose, galactose, mannose, glucosamine and galactosamine.

2. The enzyme of claim 1, wherein said enzyme has a greater activity in the presence of magnesium than either manganese or cobalt.

3. The enzyme of claim 1, wherein said enzyme requires magnesium for optimal activity.

4. The enzyme of claim 1, wherein said enzyme activity requires a phosphate donor, wherein said phosphate donor is ATP.

5. The enzyme of claim 1, wherein said enzyme activity is inhibited by sulhydryl group inhibitors.

* * * * *